(12) United States Patent
Gerber et al.

(10) Patent No.: US 6,557,695 B2
(45) Date of Patent: May 6, 2003

(54) APPARATUS AND METHOD FOR INSPECTING NON-ROUND CONTAINERS

(75) Inventors: Stephen M. Gerber, Petersburg, MI (US); George A. Nickey, Maumee, OH (US); Noel D. Wendt, Toledo, OH (US)

(73) Assignee: Owens-Brockway Glass Container Inc., Toledo, OH (US)

( * ) Notice: Subject to any disclaimer, the term of this patent is extended or adjusted under 35 U.S.C. 154(b) by 0 days.

(21) Appl. No.: 09/919,705

(22) Filed: Aug. 1, 2001

(65) Prior Publication Data

US 2003/0034227 A1 Feb. 20, 2003

(51) Int. Cl.$^7$ .............................................. B65G 29/00
(52) U.S. Cl. .............................. 198/473.1; 198/803.11; 198/867.08; 294/87.1
(58) Field of Search .................. 198/473.1, 803.11, 198/867.08, 479.1, 867.05; 294/104, 106, 87.1

(56) References Cited

U.S. PATENT DOCUMENTS

| | | | |
|---|---|---|---|
| 1,109,541 A | 9/1914 | Pease et al. | |
| 2,349,638 A | 5/1944 | Schreiber | |
| 2,393,188 A | 1/1946 | Reynolds | |
| 2,682,802 A | 7/1954 | Fedorchak et al. | |
| 2,938,620 A | 5/1960 | Waters | |
| 3,133,638 A | 5/1964 | Calhoun | |
| 3,279,599 A | 10/1966 | Drennan | |
| 3,313,409 A | 4/1967 | Johnson | |
| 3,351,198 A | 11/1967 | Wyman | |
| 3,382,974 A | 5/1968 | Mayeux | |
| 3,556,279 A | * 1/1971 | Cotter | 198/29 |
| 3,599,780 A | 8/1971 | Sorbie | |
| 3,601,616 A | 8/1971 | Katsumata | |
| 3,651,937 A | 3/1972 | Kronseder | |
| 3,710,928 A | * 1/1973 | Van Zijp | 198/210 |
| 3,811,567 A | 5/1974 | Tomita et al. | |
| 3,827,812 A | 8/1974 | Heimann | |
| 3,941,686 A | 3/1976 | Juvinal | |
| 3,963,348 A | 6/1976 | Nakatani et al. | |
| 3,975,260 A | 8/1976 | Peyton et al. | |
| 4,029,958 A | 6/1977 | Wright | |
| 4,041,672 A | 8/1977 | Gularte | |
| 4,055,252 A | 10/1977 | Klamm et al. | |
| 4,075,086 A | 2/1978 | Marsh, III et al. | |
| 4,124,112 A | 11/1978 | Mohney et al. | |
| 4,159,762 A | 7/1979 | Bulwith | |
| 4,172,524 A | 10/1979 | Holm et al. | |
| 4,200,183 A | 4/1980 | Riggs | |
| 4,230,219 A | 10/1980 | Pezzin et al. | |

(List continued on next page.)

OTHER PUBLICATIONS

U.S. patent application No. 09/679,584, filed Oct. 4, 2000.

*Primary Examiner*—Douglas Hess

(57) ABSTRACT

An apparatus for inspecting non-round containers includes a pair of carriages coupled to associated motors for rotation independently of each other on a common axis. Each carriage carries a corresponding plurality of semi-circular gripping fingers, which may be moved toward and away from each other by controlled rotation of the carriages. The fingers are widely separated from each other to accept non-round containers at an in-feed station, and to permit removal of the containers at out-feed and reject stations. For transporting the containers between stations, the finger are brought closely together to grip the containers for indexing, and springs on one of the carriages resiliently urge the associated fingers toward the fingers on the opposing carriage for accommodating size variations among the containers. At inspection stations, the fingers are moved slightly away from each other, but remain together so as to define a circular perimeter for capturing the non-round body and confining the body of the container during rotation. The container may be rotated by a drive roller engaged with the cylindrical container finish. The container finish can be inspected, as can portions of the sidewall, base and heel.

8 Claims, 4 Drawing Sheets

U.S. PATENT DOCUMENTS

| | | |
|---|---|---|
| 4,241,256 A | 12/1980 | Tagaya et al. |
| 4,378,493 A | 3/1983 | Dorf et al. |
| 4,391,372 A | 7/1983 | Calhoun |
| 4,433,785 A | 2/1984 | Riggs |
| 4,442,934 A | 4/1984 | Dorf |
| 4,460,212 A * | 7/1984 | Montferme ................ 294/115 |
| 4,579,227 A | 4/1986 | Miller |
| 4,596,107 A | 6/1986 | Pfleger, Sr. |
| 4,601,395 A | 7/1986 | Juvinall et al. |
| 4,629,389 A * | 12/1986 | Kontz ....................... 414/433 |
| 4,636,635 A | 1/1987 | Krönseder |
| 4,651,879 A * | 3/1987 | Harris et al. ................ 209/523 |
| 4,731,649 A | 3/1988 | Chang et al. |
| 4,776,448 A * | 10/1988 | Kulig ...................... 198/477.1 |
| 4,852,415 A | 8/1989 | Bogatzki et al. |
| 4,912,318 A | 3/1990 | Kajiura et al. |
| 4,915,237 A | 4/1990 | Chang et al. |
| 5,082,105 A * | 1/1992 | Tincati .................... 198/473.1 |
| 5,253,910 A * | 10/1993 | Perrier ....................... 294/116 |
| 5,392,928 A | 2/1995 | Nickey et al. |
| 5,404,227 A | 4/1995 | Sumita et al. |
| 5,459,313 A | 10/1995 | Schrader et al. |
| 5,460,591 A * | 10/1995 | Sand ........................... 493/88 |
| 5,719,679 A | 2/1998 | Shimizu et al. |
| 5,772,001 A | 6/1998 | Otruba et al. |
| 5,826,400 A * | 10/1998 | Martin et al. ................. 53/367 |
| 6,025,909 A | 2/2000 | Juvinall et al. |

\* cited by examiner

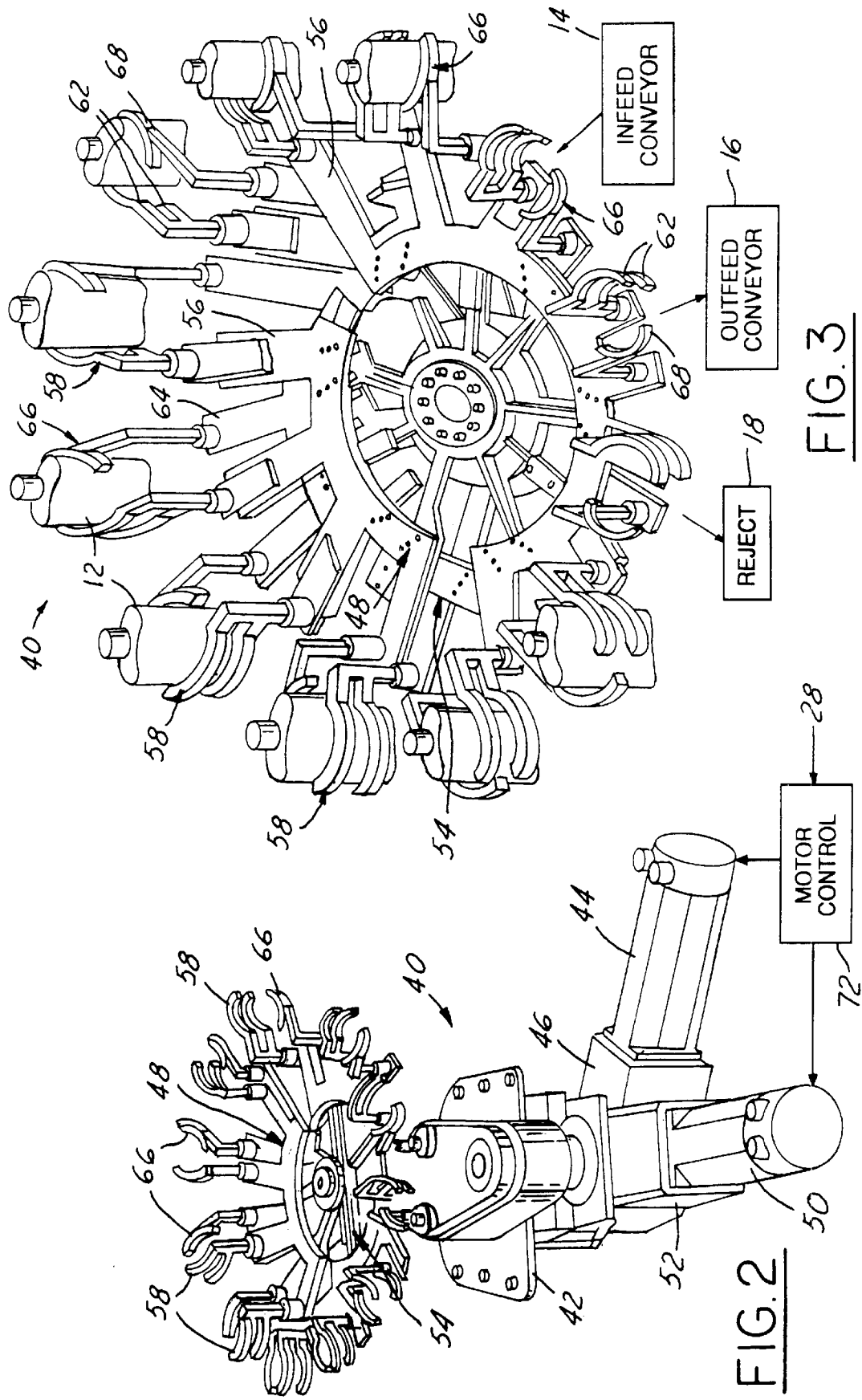

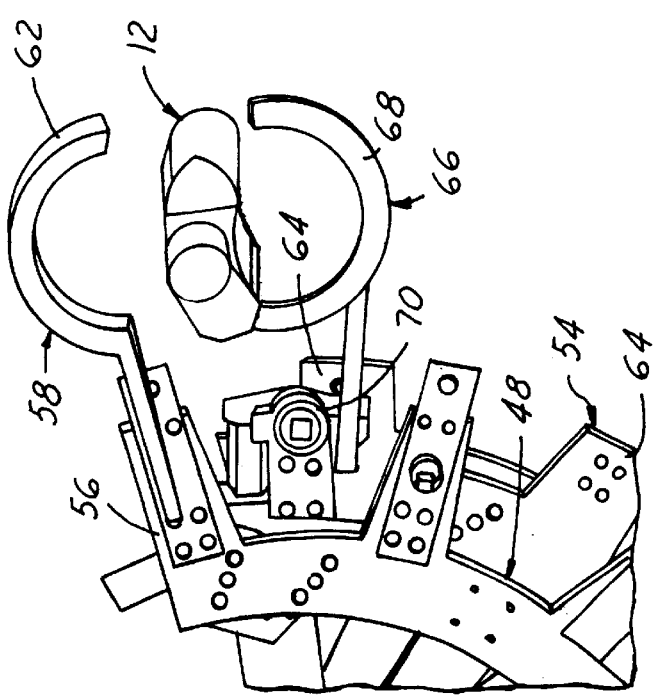
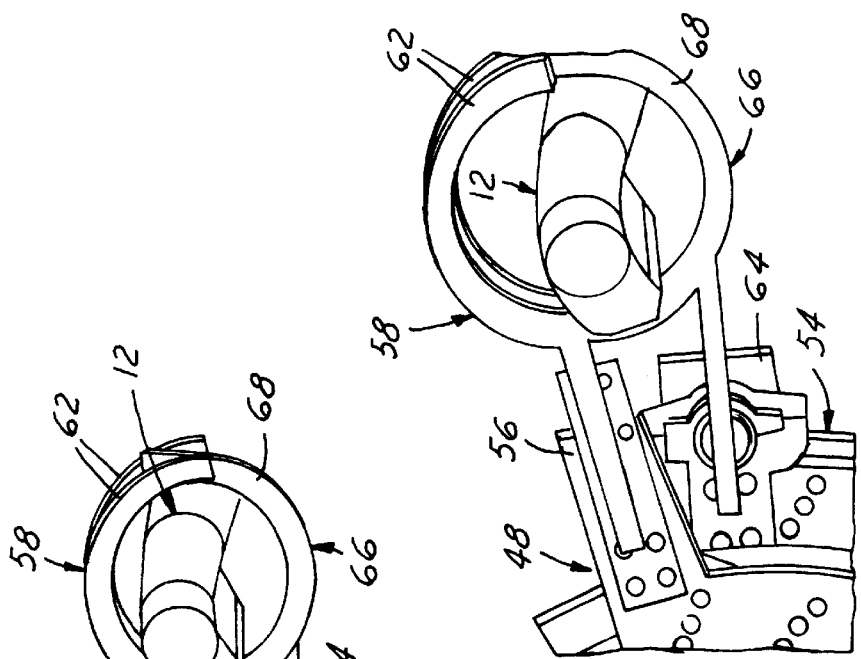

APPARATUS AND METHOD FOR INSPECTING NON-ROUND CONTAINERS

The present invention is directed to inspection of glassware articles such as glass containers, and more particularly to an apparatus and method for transporting non-round containers through a series of inspection stations.

BACKGROUND OF THE INVENTION

In the manufacture of glassware, such as glass containers, various anomalies or variations can occur that affect commercial acceptability of the containers. These anomalies, termed "commercial variations," can involve dimensional characteristics of the container such as at the container finish, surface characteristics that can affect acceptable operation of the container such as surface variations at the container sealing surface, or variations such as stones or checks within the container finish, sidewall or bottom. It is also conventional practice to mold indicia on each container indicative of the mold of origin of the container for inspection and quality control purposes. U.S. Pat. No. 4,378,493 illustrates a starwheel-type conveyor or transporter for accepting containers in sequence from an in-feed conveyor and transporting the containers through a series of inspection stations. At at least some of the inspection stations, the container is held in position and rotated about its central axis while being electro-optically inspected for commercial variations and/or mold code. The term "inspection" is used to its broadest sense to encompass any optical, electro-optical, mechanical or electrical observation of or engagement with the container to measure or determine a potentially variable characteristic, including but not necessarily limited to mold codes and commercial variations.

U.S. application Ser. No. 09/679,584 filed Oct. 4, 2000 and assigned to the assignee hereof, discloses an apparatus for indexing glassware through a series of angularly spaced stations. The apparatus includes first and second arrays of glassware gripping fingers mounted on associated carriers that are rotatable on a common axis, both conjointly and with respect to each other. Each carrier is connected to an associated servo motor, which in turn are connected to a controller for rotating the carriers with respect to each other to grip and release glassware between the fingers, and to rotate the carriers conjointly to index the glassware between apparatus stations. Drive rollers are located at at least some of the stations, and are pivotal into and out of position for rotating the containers about their axes for inspection and other purposes. The apparatus and method disclosed in such patent are particularly well suited for inspection of round containers, but are not as well suited for inspection of non-round containers such as flasks, which must be tightly gripped for transport between stations but loose gripped at the stations to permit rotation of the containers about their axes. It is a general object of the present invention to provide a method and apparatus for transport and inspection of non-round containers.

U.S. Pat. No. 4,124,112, assigned to the assignee hereof, discloses a transporter for indexing non-round containers through a circumferential array of inspection stations. The containers are loosely encircled by cam-operated mechanisms and slid along a plate between inspection stations. Thus, the apparatus disclosed in the noted patent is not suited for use in conjunction with a container transport and inspection system in which the containers must be tightly gripped and transported between stations, as distinguished from being loosely gripped and slid along a support plate.

SUMMARY OF THE INVENTION

Apparatus for inspecting non-round containers at a plurality of inspection stations in accordance with a presently preferred embodiment of the invention includes first and second circumferential arrays of glassware gripping fingers disposed in pairs having opposed partcircular arms. The first and second finger arrays are mounted on respective first and second carriers that are rotatable on a common axis. First and second motors are respectively coupled to the first and second carriers for rotating the carriers independently of each other on their common axis to close the part-circular arms about a container body tightly to grip the container body, to transport the container between inspection stations, partially to open the arms to permit rotation of the container at an inspection station while confining the body of the container, and fully to open the fingers with respect to each other to permit insertion and removal of a container between the fingers. A drive roller may engage the finish of the container at at least one of the inspection stations to rotate the container about the axis of its finish while the container body is confined by the fingers.

A method of transporting non-round containers, from a load station through at least one inspection station to an unload station in accordance with a preferred embodiment of the invention, includes providing first and second circumferential arrays of glassware gripping fingers and positioning the fingers in opposed pairs having part-circular arms. At least one of the arrays is moved toward the other at the load station to close the part-circular arms tightly around a container body. The container is transported to the inspection station by rotating the arm arrays simultaneously on a common axis. At least one of the arrays is then moved away from the other at the inspection station partially to open the arms to permit rotation of the container while confining the container between the arms. At least one of the arrays is moved away from the other at the unload station fully to open the arms and permit removal of the container from between the fingers.

BRIEF DESCRIPTION OF THE DRAWINGS

The invention, together with additional objects, features and advantages thereof, will be best understood from the following description, the appended claims and the accompanying drawings in which:

FIG. 2 is a perspective view of the carrier drive unit subassembly in the conveyor of FIG. 1;

FIG. 3 is a fragmentary perspective view of the carrier subassembly of FIG. 2 gripping non-round containers for purpose of transport between stations;

FIGS. 5A, 5B and 5C are fragmentary perspective views that illustrate a portion of the conveyor configured for receiving or releasing containers at in-feed, out-feed or reject stations (FIG. 5A), tightly gripping the container for transport between stations (FIG. 5B), and loosely confining the container for rotation at an inspection station (FIG. 5C).

DETAILED DESCRIPTION OF PREFERRED EMBODIMENTS

The disclosure of above-noted U.S. application Ser. No. 09/679,584 filed Oct. 4, 2000 and assigned to the assignee hereof, is incorporated herein by reference.

Figure 1:
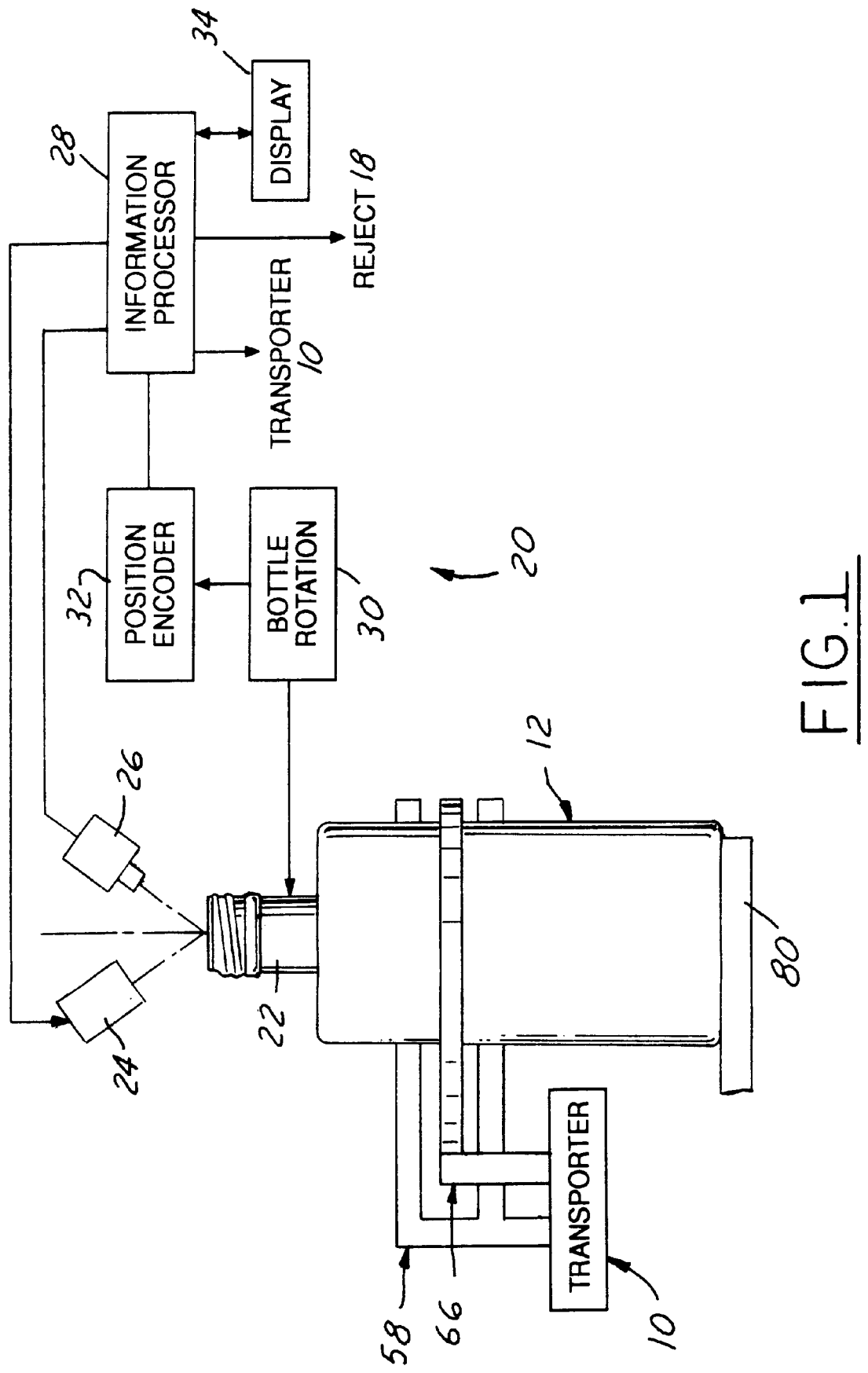
FIG. 1 is a schematic diagram for inspecting the sealing surface of containers transported through an inspection station by a conveyor in accordance with a presently preferred embodiment of the invention.
Figure 4:
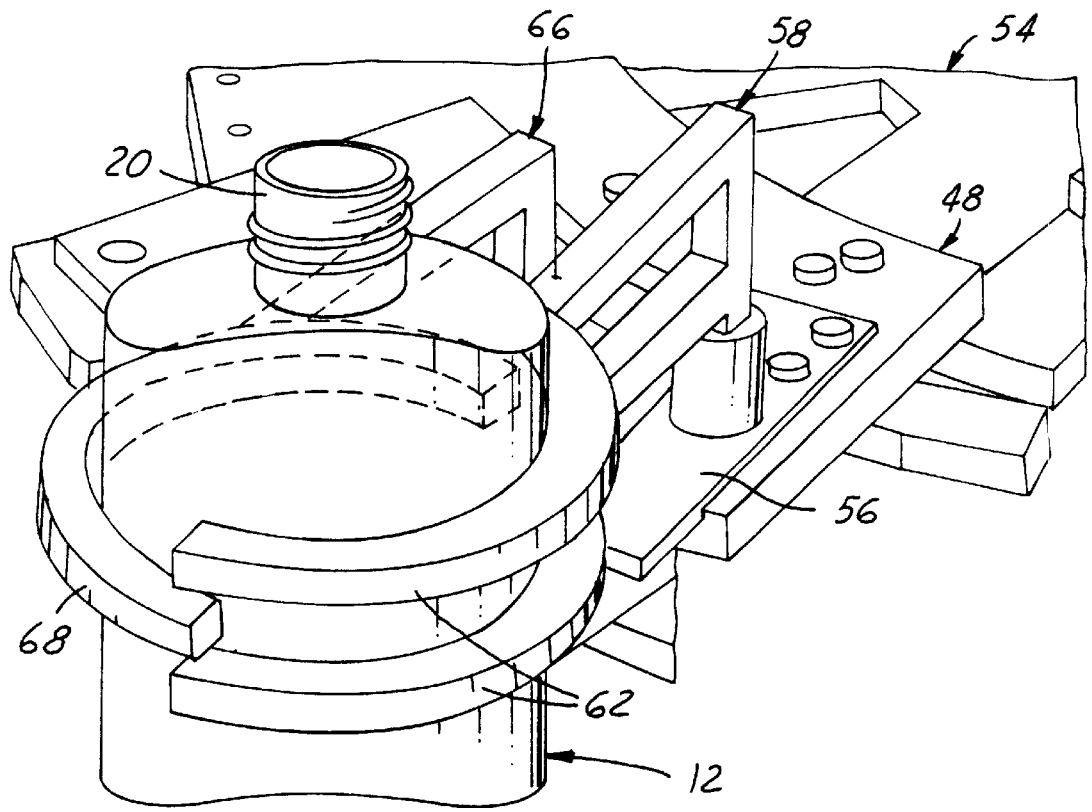
FIG. 4 is a fragmentary perspective view of the conveyor tightly gripping a non-round container body for transport between stations.

FIG. 1 of the present application illustrates a conveyor or transporter 10 for transporting non-round containers 12 between and through a plurality of angularly spaced stations. These stations preferably are spaced at equal angular increments around a common axis. An in-feed conveyor 14 (FIG. 3), such as an endless belt conveyor, brings containers 12 in sequence to one of the stations. In general, transporter 10 grips container 12 as they are presently on in-feed conveyor 14, and incrementally transports the containers to each station in turn around the apparatus. At at least some of the stations, containers 12 are held in position and rotated about their axes for inspection or other purposes. Containers 12 are ultimately indexed to an out-feed conveyor 16 (FIG. 3), or a cullett or reject chute 18 for removing containers that do not pass inspection, or to a sampling or other device for sampling containers from a specific mold, for example. The in-feed, out-feed and reject conveyors are illustrated in greater detail in the above-referenced U.S. Application.

In the preferred implementation of the present invention, the containers are subject to inspection for commercial variations at at least one of the stations between the in-feed and reject stations. FIG. 1 illustrates an exemplary station 20 for inspecting a container finish 22. A light source 24 and a camera 26 are coupled to an information processor 28 for directing light energy onto the container finish and scanning the camera at increments of container rotation. A container rotation device 30, such as a drive roller, is positioned to engage container finish 22 and to rotate the container about the axis of the container finish while the container is held in fixed position by conveyor 10. An encoder 32 is coupled to container rotation mechanism 30 and to information processor 28 to provide to the information processor signals indicative of increments of container rotation. Such container rotation increments may comprise increments of angular position, or time increments as the container is rotated at constant velocity. Information processor 28 is also connected to a display 34 for displaying the results of the inspection operation to an operator, and to conveyor 10 and reject station 18 for controlling operation of the conveyor and reject station. Container finish inspection station 20 is disclosed in greater detail in U.S. Pat. No. 6,025,909. Other container dimensional or other parameters can also be inspected as shown, for example, in U.S. Pat. No. 2,682,802 (finish check detection), U.S. Pat. No. 3,880,750, U.S. Pat. No. 5,896,195 or EP 0,961,113 (sealing surface inspection), U.S. Pat. Nos. 4,378,493, 4,378,495, 4,584,469, 5,233,186, 5,291,271 or 5,637,864 (container sidewall inspection), or EP 0,764,846 (container bottom inspection). Successive containers can also be inspected to determine or read the code molded into the container for indicating container mold of origin, as illustrated for example in U.S. Pat. No. 4,644, 151. Although electro-optical inspection techniques are currently preferred, the apparatus and method of the present invention can also accommodate mechanical inspection techniques, such as illustrated in U.S. Pat. No. 5,414,939 in which the container is contacted by one or more rollers or fingers as it is rotated about its axis. Electrical inspection techniques, as illustrated, for example, in U.S. Pat. No. 4,046,258, are also envisioned.

Transporter 10 in accordance with the present invention includes a carrier drive unit or subassembly 40 (FIGS. 2 and 3), mounted on a fixed or moveable support frame. Carrier drive unit 40 includes a central support 42 that is mounted on the frame. A first rotary electric servo motor 44 and an associated gear box 46 are mounted on the underside of support 42, and are coupled to a shaft that extends upwardly through the support. The axis of rotation of the shaft defines the central axis of carrier drive unit 40 and transporter 10. The upper end of the shaft is coupled to a first or upper carrier 48. A second rotary electric servo motor 50 and an associated gear box 52 are mounted beneath support 42 laterally offset from the axis of the shaft. Gear box 52 is rotatably coupled to a second or lower carrier 54. Thus, first or upper carrier 48 is rotatable about the axis of the shaft under control of motor 44 and gear box 46, while second or lower carrier 54 is rotatable about the axis of the shaft under control of motor 50 and gear box 52 independently of rotation of upper carrier 48.

Referring to FIGS. 3–5C, upper carrier 48 has a plurality of angularly equally spaced radially extending legs 56. A container gripping finger 58 is secured to the outer end of each leg 56. Each finger 58 is inverted L-shaped in elevational view, having a straight vertical leg and a pair of vertically spaced radially extending horizontal legs 62. Horizontal legs 62 are semi-circular in geometry, as best seen in FIGS. 5A–5C. Likewise, lower carrier 54 includes a plurality of angularly equally spaced radially extending legs 64, at the outer ends of which are mounted a corresponding container-gripping finger 66. Each finger 66 is generally inverted L-shape, in elevational view having a straight vertical leg secured to radial leg 56 and a radially extending semi-circular leg 68 that is disposed in assembly between legs 62 of each finger 58. A coil spring 70 is coupled to each finger 66 rotatably to bias each finger 66 toward the associated opposing finger 58 and thereby accommodate size variations among the bodies of containers 12 transported by the conveyor. A layer or coating of resilient elastic material such as polyurethane is provided on the inside surface of each leg 62, 68 for engaging the containers without damage to the containers and to enhance frictional gripping of the containers for transport between stations. Information processor 28 (FIG. 1), is connected through a motor control unit 72 (FIG. 2) for controlling operation of motors 44, 50, and thereby controlling rotation of upper and lower carriers 48, 54, as will be described.

In operation, with the containers at the various inspection stations resting on a support 80 (FIG. 1), at least one of the carriers 48, 54, and preferably both of the carriers, are simultaneously rotated about their common axes, by control of motors 44, 50 (FIG. 2), to move fingers 58, 66 away from each other (FIG. 5A) to accept new containers from in-feed conveyor 14 (FIG. 3), deposit containers on out-feed conveyor 16, and release containers at reject station 18. At least one of the carriers 48, 54, and preferably both carriers, are then simultaneously rotated about their common axes toward each other tightly to grip all containers between fingers 58,66 (FIG. 5B). The carriers are then simultaneously rotated by their associated motors, in the counterclockwise direction in FIG. 3, incrementally to transport the containers between adjacent angularly spaced stations. It will be noted that there is no support plate or the like between supports 80 at the inspection stations and along which the containers may be slid. Thus, it is necessary tightly to grip the containers for transport between stations, and the resilient layers on the fingers enhance such gripping action. When the containers are at the next stations, at least one of the carriers 48, 54, and preferably both carriers, are then simultaneously rotated to move fingers 58, 66 slightly away from each other (FIG. 5C) to release the containers for rotation while confining the bodies of the containers during rotation. The finish of the container or containers under inspection can be engaged by associated drive rollers 30 (FIG. 1) for rotating the containers about their axes during the inspection process. (Containers may, of course, be inspected while in stationary position at some of the inspection stations, if desired.) After inspection has been completed at all inspection stations, fingers 58, 66 are moved to the position of FIG. 5A by rotation of the associated carriers so that inspected containers are released to the reject or out-feed conveyors and new containers are received for inspection. These steps are repeated in sequence for transporting a continuing series of containers through the successive stations.

Details of upper carriage 48, lower carriage 54, support 80, mounting of arms 58, 66 on the carriers, coupling of motors 44, 50 to the carriers, mounting of subassembly 40 on a support frame, and mounting of drive roller 30 for engagement with the container finish are disclosed in the above-referenced copending U.S. Application.

There have thus been disclosed an apparatus and method for indexing glassware, such as containers, through a series of stations, such as container inspection stations, that fully satisfy all of the objects and aims previously set forth. A number of modifications and variations have been discussed. For example, a container under inspection could be rotated other than by rollers that engage the finish, such as by gripping the container at an inspection station between top and bottom pads, one or both of which are driven to rotate the container. Other modifications and variations will readily suggest themselves to persons of ordinary skill in the art. The invention is intended to embrace all such modifications and variations as fall within the spirit and broad scope of the appended claims.

What is claimed is:

1. Apparatus for inspecting containers, having a non-round body and a cylindrical finish, at a plurality of inspection stations, comprising:

first and second circumferential arrays of glassware gripping fingers, said fingers being disposed in pairs having opposed part-circular arms, first and second carriers respectively mounting said first and second finger arrays for rotation about a common axis, and first and second motors respectively coupled to said first and second carriers for rotating said carriers independently of each other about said common axis to close said part-circular arms about a container body, transport the container between inspection stations, partially open said arms to permit rotation of the container while confining the body of the container, and fully open the fingers with respect to each other to permit removal of a container from between said fingers.

2. The apparatus set forth in claim 1 further comprising a drive roller to engage a container finish at at least one of said inspection stations and rotate the container about the axis of the finish.

3. The apparatus set forth in claim 1 further comprising springs carried by one of said carriers and engaged with the fingers on that carrier for resiliently urging such fingers toward the fingers on the other carrier to accommodate variation in container size.

4. The apparatus set forth in claim 1 wherein said part-circular arms comprise semicircular arms.

5. The apparatus set forth in claim 1 wherein said first and second motors comprise electric motors, and wherein said apparatus includes control electronics coupled to said electric motors for rotating said carriers about said common axis independently of each other.

6. A method of transporting non-round containers from a load station through at least one inspection station to an enclosed station, which comprises the steps of:

(a) providing first and second circumferential arrays of glassware gripping fingers on respective first and second independently movable carriers, (b) positioning said fingers in pairs having opposed part-circular arms, (c) moving at least one of said arrays toward the other at said load station to close said part-circular arms tightly around a container body, (d) transporting the container to the inspection station by rotating said arm arrays simultaneously on a common axis, (e) moving at least one of said arrays away from the other at said inspection stations partially to open said arms to permit rotation of the container while confining the container between said arms, and (f) moving at least one of said arrays away from the other at said unload station fully to open said arms and permit removal of the container from between said fingers.

7. The method set forth in claim 6 wherein said step (c) comprises rotating both of said arrays simultaneously toward each other, wherein said step (e) comprises rotating both of said arrays simultaneously away from each other, and wherein said step (f) comprises moving both of said arrays simultaneously away from each other.

8. The method set forth in claim 6 wherein said step (a) includes providing semicircular arms on said fingers.

\* \* \* \* \*